April 5, 1966 THEW Pat. 2,616
APPLE TREE
Filed Sept. 16, 1964
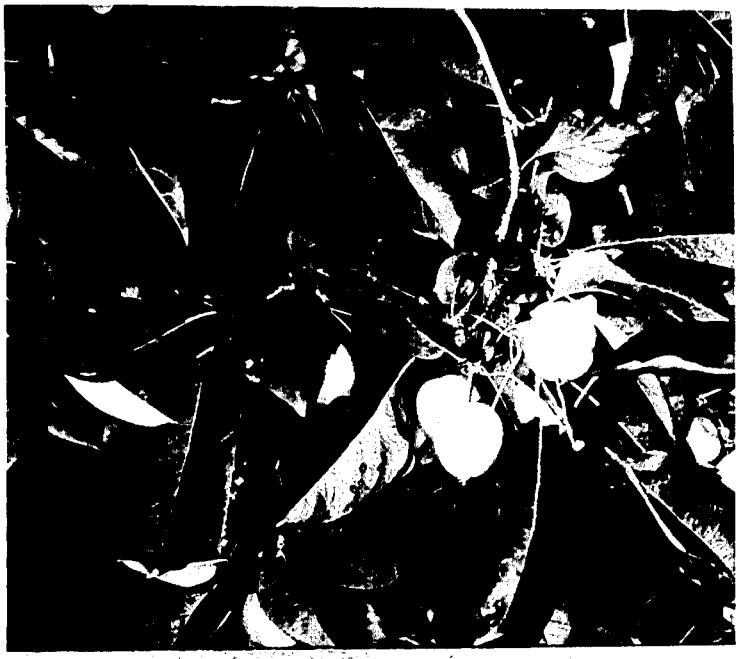
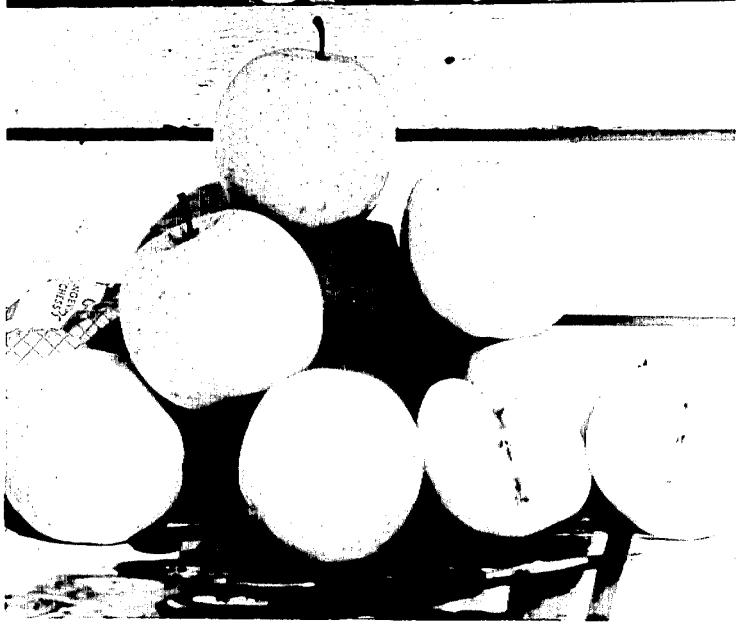
Inventor.
Gerald R. Thew
By: Robb & Robb
Attorneys.

United States Patent Office

Plant Pat. 2,616
Patented Apr. 5, 1966

2,616
APPLE TREE

Gerald R. Thew, % Thew Orchards, La Grangeville, N.Y.

Filed Sept. 16, 1964, Ser. No. 397,045
1 Claim. (Cl. Plt.—34)

The present invention relates to a new and distinct variety of apple tree which was discovered by me as a seedling of unknown parentage in my cultivated orchard in central Dutchess County, near La Grangeville, New York.

At the time of my discovery aforementioned, I was growing various varieties of apple trees, including the varities known as "Golden Delicious," "McIntosh," "Cortland," and "Red Delicious" (all unpatented). My attention was attracted to one particular tree growing almost in the row of a small orchard of about one acre in size, on the edge of my main orchard which covered about one hundred twenty-five (125) acres. I observed that this particular tree was full of fruit still hanging on the tree in the month of December, even after freezing weather, and long after the fruit of all the other trees had been picked or had fallen. The fruit of this particular tree just referred to had good size and looked like the fruit of "Golden Delicious," but after further observations and tests, it was found to be superior in many respects for cooking, eating, shipping and storage.

Continued observations of the original seedling, and of progeny thereof reproduced on my behalf by both budding and grafting at Dansville, New York, have convinced me that it is probably a seedling of "Golden Delicious" but definitely distinct therefrom and from all other varieties of which I am aware, as evidenced by a unique combintion of the following features which are outstanding therein:

(1) A general similarity to "Golden Delicious";

(2) Abundant and regular fruit production;

(3) A prolonged tendency of the fruit to hang on the tree much longer than other varieties, including "Golden Delicious" when grown under the same conditions;

(4) The ability of the fruit to color up well while in storage or when taken out of storage, if originally picked a little green;

(5) Good keeping qualities of the fruit both in storage and on the shelf, remaining firm, without shriveling, after removal from storage longer than the fruit of "Golden Delicious";

(6) Greater resistance to bruises, with resulting superior handling, packing and shipping qualities due to the firmer fruit flesh;

(7) Small fruit cores, with few seeds;

(8) Excellent fruit flavor, which is somewhat more tart than the fruit of "Golden Delicious";

(9) A smoother and more waxy fruit skin and freedom from rust; and

(10) An attractive appearance of the fruit as achieved by its bright yellow ground color and sometimes having a reddish blush, generally resembling the fruit of "Golden Delicious."

Asexual reproduction by both budding and grafting, as performed at Dansville, New York, shows that the foregoing characteristics and distinctions of my new variety come true to form and are established and transmitted through succeeding propagations.

The accompanying drawing shows a portion of a typical tree of my new variety, with typical leaves and fruit depicted thereon, ae well as typical fruit specimens depicted on an enlarged scale, with the specimens arranged in different positions to better show the form and color of the fruit, and with one specimen depicted in cross-section to expose the flesh and other details.

The following is a detailed description of my new variety with color terminology in accordance with Koster's Color Guide, except where general color terms of ordinary dictionary significance are obvious:

Locality where grown and observed: Arthursburg, New York.

Dates of first and last pickings: About October 15 and November 1, respectively.

Tree: Medium size; medium vigorous; spreading; tall; with central leader; slow growing; hardy; very productive; regular bearer annually.

*Trunk.*—Medium stocky; medium smooth.

*Branches.*—Slender; smooth; much-branched. Color—brown. Lenticels—few.

*Leaves.*—Large; from 4½ inches to 5¼ inches long and from 2 inches to 3 inches wide; medium thickness. Color—near Taxus Green, Plate 81. Margin—crenate.

Flowers: Dates of first and full bloom—same as "Golden Delicious."

Fruit:

*Maturity date.*—Same as "Golden Delicious."

*Size.*—Axial diameter—2¾ inches. Transverse diameter—2¾ inches.

*Form.*—Uniform; symmetrical; regular; globose; slightly ribbed.

*Cavity.* — Symmetrical. Depth — ½ inch. Breadth—⅛ inch.

*Basin.*—Symmetrical; rounded; narrow base; even; glabrous.

*Stem.*—Clubbed; slender; pubescent; bracts wanting. Length—from ¾ inch to 1 inch.

*Calyx.*—Open; segments persistent; ¼ inch long; separated; prostrate; reflexed from base; both outer surface and inner surface pubescent.

*Eye.*—Medium size; open.

*Skin.*—Thin; tough; smooth; waxed. Dots—conspicious; few; small; depressed; ruptured; stellate; color—brown; distribution—even. Ground color—near Lemon Yellow, Plate 7. Color markings—blushed with near Cardinal Red, Plate 27, some years, but blush is absent some years. Bloom—scant. Scarfskin—wanting. General color effect—yellow, with reddish blush.

Flesh:

*Color.*—Near Creamy White, Plate 2.

*Texture.*—Firm.

*Flavor.*—Best; somewhat more tart than the fruit of "Golden Delicious."

Core: Small; symmetrical.

*Bundles.*—Inconspicuous. Color—yellowish.

*Cross section.*—Indistinct.

*Carpellary area.*—Indistinct; small.

*Calyx tube.*—Glabrous; cone-shaped.

*Stem of funnel.*—Short.

*Depth of tube to shoulder.*—¼ inch.

*Styles.*—Present; distinct toward base; pubescent throughout.

*Stamens.*—Distinct; basal.

*Axillary cavity.*—Wanting.

*Seed cells.* — Cell walls — approximate; thin. Length—½ inch.

*Longitudinal section.*—Narrowly ovate.

*Cross section.*—Narrow.

Seeds: Vary from few to none; sometimes 5 imperfect, with no more than 2 seeds in one cell.

Use: Market; local; dessert; culinary.

Keeping quality: Excellent; keeps well as long as 6½ months in ordinary storage.

Disease resistance: Good resistance to scab, as determined from comparison with other varities grown under the same conditions in central Dutchess County, New York.

I claim:

A new and distinct variety of apple tree, substantially as herein shown and described, characterized particularly as to novelty by the unique combination of a general similarity to "Golden Delicious," abundant and regular fruit production, a prolonged tendency of the fruit to hang on the tree much longer than other varieties, including "Golden Delicious" when grown under the same conditions, the ability of the fruit to color up well while in storage or when taken out of storage, if originally picked a little green, good keeping qualities of the fruit both in storage and on the shelf, remaining firm, without shriveling, after removal from storage longer than the fruit of "Golden Delicious," greater resistance to bruises, with resulting superior handling, packing and shipping qualities due to the firmer fruit flesh, small fruit cores, with few seeds, excellent fruit flavor, which is somewhat more tart than the fruit of "Golden Delicious," a smoother and more waxy fruit skin and freedom from rust, and an attractive appearance of the fruit as achieved by its bright yellow ground color, and sometimes having a reddish blush, generally resembling the fruit of "Golden Delicious."

No references cited.

ABRAHAM G. STONE, *Primary Examiner.*